United States Patent
Bala

(10) Patent No.: US 9,623,134 B1
(45) Date of Patent: Apr. 18, 2017

(54) STERILIZATION TEST STRIP

(71) Applicant: Dana Products, Inc., Franklin Park, IL (US)

(72) Inventor: Harry Bala, South Barrington, IL (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 14/852,230

(22) Filed: Sep. 11, 2015

Related U.S. Application Data

(63) Continuation of application No. 13/432,807, filed on Mar. 28, 2012, which is a continuation-in-part of application No. 13/031,491, filed on Feb. 21, 2011, now abandoned.

(51) Int. Cl.
*G01N 31/22* (2006.01)
*A61L 2/28* (2006.01)
*G01K 1/02* (2006.01)

(52) U.S. Cl.
CPC . *A61L 2/28* (2013.01); *G01K 1/02* (2013.01)

(58) Field of Classification Search
CPC ....... G01N 31/226; G01N 33/525; A61L 2/28
USPC ......................................................... 422/420
See application file for complete search history.

(56) References Cited

U.S. PATENT DOCUMENTS

| | | | |
|---|---|---|---|
| 3,313,266 A | 4/1967 | Kelson | |
| 3,341,238 A | 9/1967 | White | |
| 3,652,249 A | 3/1972 | White | |
| 3,981,683 A | 9/1976 | Larsson et al. | |
| 4,448,548 A * | 5/1984 | Foley | G01N 31/226 252/408.1 |
| 5,158,363 A * | 10/1992 | Speelman et al. | A61L 2/28 116/207 |
| 5,378,430 A * | 1/1995 | Nieves et al. | A61L 2/28 116/207 |
| 5,602,804 A * | 2/1997 | Haas | G01K 3/04 116/206 |
| 5,709,472 A * | 1/1998 | Prusik et al. | G01K 3/04 116/219 |
| 7,811,516 B2 | 10/2010 | Bala | |
| 2009/0047176 A1 * | 2/2009 | Cregger et al. | A61L 2/28 422/28 |
| 2011/0275159 A1 * | 11/2011 | Landgrebe et al. | A61L 2/28 436/1 |

FOREIGN PATENT DOCUMENTS

WO  WO9524622 A1 *  2/1995

OTHER PUBLICATIONS

Sigma-Aldrich, "Whatman qualititative filter apper, Grade 1," 2015, http://www.sigmaaldrich.com/catalog/product/aldrich/274844?lang=en&region=US.*

"Filter Papers and Membranes," http://www.chimica.unipd.it/nicola.tiso/pubblica/_private/Utile/catalogo%20whatman.pdf.*

* cited by examiner

*Primary Examiner* — Jill Warden
*Assistant Examiner* — Brittany Fisher
(74) *Attorney, Agent, or Firm* — Levenfeld Pearlstein, LLC

(57) ABSTRACT

A sterilization test strip includes a temperature sensitive material, which liquefies and travels along a wicking element when exposed to steam at a predetermined temperature for a predetermined period time to reach a marker to indicate that an acceptable level of sterilization has not occurred.

14 Claims, 1 Drawing Sheet

STERILIZATION TEST STRIP

CROSS-REFERENCE TO RELATED APPLICATION DATA

This application a continuation of U.S. patent application Ser. No. 13/432,807, filed Mar. 28, 2012 entitled, "STERILIZATION TEST STRIP", which is a continuation in part of U.S. patent application Ser. No. 13/031,491, filed Feb. 21, 2011 entitled, "STERILIZATION TEST STRIP", the content of which are incorporated fully by reference herein.

BACKGROUND OF THE INVENTION

It is well known that heat destroys microorganisms. The presence of moisture accelerates this destruction by denaturing or coagulation of the proteins making up the microorganisms. Most microorganisms contain sufficient water so that moderate heat alone, e.g. 80° C.-100° C., will destroy the microorganism. Many bacterial spores, on the other hand, contain substantially no water and require elevated temperatures in excess of 150° C. for their destruction where dry heat is used. Hence, the destruction of such organisms is generally carried out in the presence of steam in autoclaves.

Such steam sterilization is generally carried out at temperatures of about 250° F. (121° C.) for at least 12 to 15 minutes or for shorter times at higher temperatures e.g. 270° F. (132° C.). Often, to ensure a sufficient safety margin, times as long as 30 minutes are used. Such long sterilization times give the operator a greater degree of confidence that steam has penetrated throughout the autoclave and among all of its contents. However, such long heat cycles are disadvantageous from the standpoint of economy of time, energy consumption, and severe shortening of the useful life of certain types of sterilized material, e.g., fabric gowns, drapes, and the like.

From time to time attempts have been made to develop sterilization indicators which permit quality control of sterilization with the confidence that all microorganisms have been destroyed. One presently used method is through the use of spore strips or samples. Spores which are particularly difficult to destroy are selected as the control standard, e.g., *Bacillus Subtilis* var. *Niger* and *Bacillus Stearothermophilus*. The spore strip or sample is placed in the autoclave with the materials to be sterilized. At the end of the sterilization cycle, the spore strip or sample is studied to determine whether it is possible to grow organisms in a suitable culture medium. Failure of the spores to reproduce indicates death of spores, and hence, adequate sterilization.

Although this control technique is accurate, it suffers from several inherent disadvantages; (1) excessive cost; (2) delay between processing and control data; (3) batch to batch variation of the spores; and (4) heat resistance of spores decreases with storage time.

Several attempts have been made to devise chemical type sterility indicators. One such product is known as Temp-Tube, and is disclosed in, for example, Kelson, U.S. Pat. No. 3,313,266, White, U.S. Pat. No. 3,341,238, and White, U.S. Pat. No. 3,652,249. The device consists of a sealed tube containing a compound with a melting point which corresponds to the sterilization temperature. The device is capable of indicating whether or not the autoclave was held at a temperature above or below the melting point for a period of time once the melting point is reached.

Other sterility indicators rely on a temperature accelerated chemical reaction to cause color change in an indicator. Though some of these devices are intended to be operative at more than one temperature/time condition, they suffer from the disadvantage that they do not match the spore kill temperature/time relationships. The thermal resistance of spores of a particular species at any temperature is characterized by its temperature coefficient. The symbol $Q_{10}$ is used to designate the temperature coefficient over a range of 10° C. It corresponds to the ratio of the death rate constant at a particular temperature to the death rate constant at a temperature 10° C. lower. Generally, the measurements are made for a fixed time interval, e.g., 9 minutes.

If the constants at any two temperatures, $t_1$, and a temperature 10° C. higher, $t_2$, are known, then $Q_{10}$ may be calculated from the equation:

$$\log Q_{10} = (10/(t_2-t_1)) \times \log(K_2/K_1)$$

wherein $t_1$ and $t_2$ are as defined and $K_1$ and $K_2$ are the respective death rate constants. Spores generally exhibit a $Q_{10}$ value of about 10.

Other sterility indicators are known. One such indicator is disclosed in Larsson, U.S. Pat. No. 3,981,683, and uses a backing strip of aluminum foil having an organic compound containing oxygen or nitrogen in contact with a wicking strip, and a cover strip overlying the organic compound and the wicking strip. The cover strip is a polymeric rate controlling film that permits water vapor to pass through at a rate sufficient to make the strip operable at a temperature to be monitored.

One drawback to the device in Larsson is that the temperature and time parameters at which the indictor indicates an acceptable level of sterilization (e.g., that the temperature has been held at a minimum value for a specified period of time) is not well controlled. As such, the indicator can indicate that the requisite level of sterilization has occurred when in fact is has not.

Another such indicator is disclosed in Foley, U.S. Pat. No. 4,448,548. The device in Foley is directed to a steam sterilization indicator in which a fusible material, in tablet form, is deposited in an embossment in an aluminum backing. A wicking strip is attached to the backing in close proximity to the fusible tablet. A clear plastic material covers the tablet and the strip and is adhered to the backing.

The melting point of the fusible tablet is depressed in the presence of saturated steam. Upon melt, the material in the tablet is absorbed by the wicking strip, producing a color front to provide an indication of the integration of time and temperature in the presence of steam. Various amounts of a binder are used in the tablet to provide a device which may be adjusted to reflect the thermal death curves of various types of microorganisms. The cover and the wick are bonded to the backing by an acrylic adhesive which also affects the rate of the indicator.

As with the Larsson device, a drawback to the device in Foley is that the temperature and time parameters at which the indictor indicates an acceptable level of sterilization is not well controlled and as such, the indicator can indicate that the requisite level of sterilization has occurred when in fact is has not.

Therefore, it is desirable to have a sterility indicator that will, in a sense, mimic spore kill. Desirably, such an indicator provides indication that an acceptable level of sterilization has been reached at specific, desired, predetermined time/temperature scenarios.

BRIEF SUMMARY OF THE INVENTION

A sterilization test strip includes a base element having an adhesive backing, and is formed from a thermally conductive material having a length and a width. In one embodiment the base element is formed from aluminum having a thickness of about 3/1000 inch (3 mils).

The base element has a recess formed therein extending along about a longitudinal centerline thereof. The recess is formed within the base material less than the length and the width of the base material.

A temperature sensitive material is deposited in the recess and a wicking material is positioned at least in part in contact with the temperature sensitive material and positioned at least in part within the recess. The wicking material extends less than the length and width of the base element.

A film is positioned over the base element adhesive backing, the wicking material and the temperature sensitive material.

A coated paper is disposed over the film. The coated paper includes a window therein. A marker is disposed on the sterilization test strip.

When exposed to steam at a predetermined temperature for a predetermined period of time, the temperature sensitive material liquefies and is drawn into the wicking material and moves to a position at or beyond the marker to indicate an acceptable level of sterilization has occurred. At temperatures below the predetermined temperature for the predetermined period of time, or at the predetermined temperature for less than the predetermined period of time, or at a temperature less than the predetermined temperature for less than the predetermined period of time, the temperature sensitive material is drawn into the wicking material and moves to a position prior to the marker to indicate that an acceptable level of sterilization has not occurred.

In one embodiment, the temperature sensitive material is phenacetin. The phenacetin can include a dye added thereto. One such dye is Nile Blue present in a concentration of about 0.01 percent by weight of the temperature sensitive material.

The film can be a cast polypropylene. The cast polypropylene has a thickness of about 2.0 to 2.2 mils. Alternatively, the cast polypropylene has a thickness of about 3.0 to 3.2 mils.

In one embodiment, the coated paper has an adhesive backing and an acrylic coating thereon. The adhesive can be an acrylic adhesive.

The test strip adheres to the performance requirements set for Class 6 emulating indictors set by American National Standards Institute (ANSI)/Association for the Advancement of Medical Instrumentation (AAMI)/International Organization for Standards (ISO) 11140.

In an embodiment, the predetermined temperature is 132° C. and the predetermined period of time is 4 minutes. In another embodiment, the predetermined temperature is 134° C. and the predetermined period of time is at least 3.5 minutes. In embodiments of the test strip, the predetermined period of time can be 3.5 minutes, 4 minutes, 5 minutes or 7 minutes. In still another embodiment, the predetermined temperature is 135° C. and the predetermined period of time is 3 minutes.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
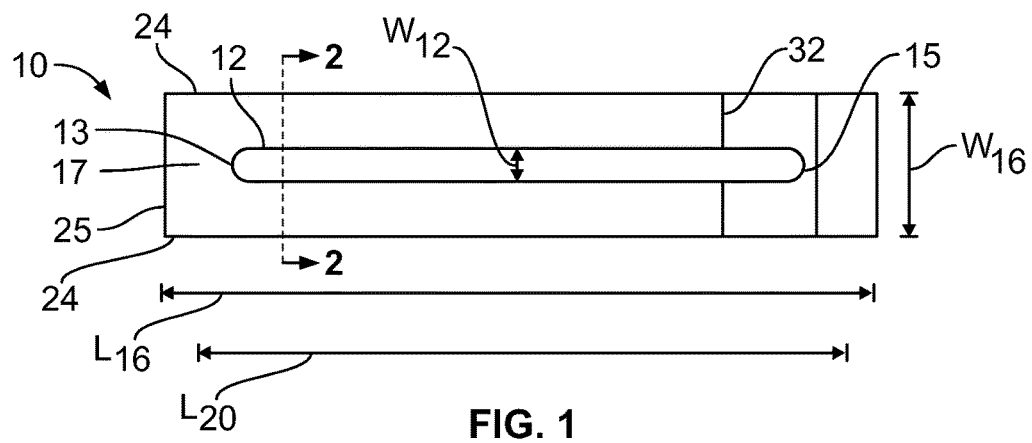
FIG. 1 is a top plan view of a sterilization test strip.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Referring now to the figures, and in particular to FIG. 1, there is shown an embodiment of a sterilization strip 10. The strip 10 has an open window 12 through which the wicking of an indictor chemical 14 can be observed to determine whether an acceptable level of sterilization has occurred as will be described below.

Figure 2:
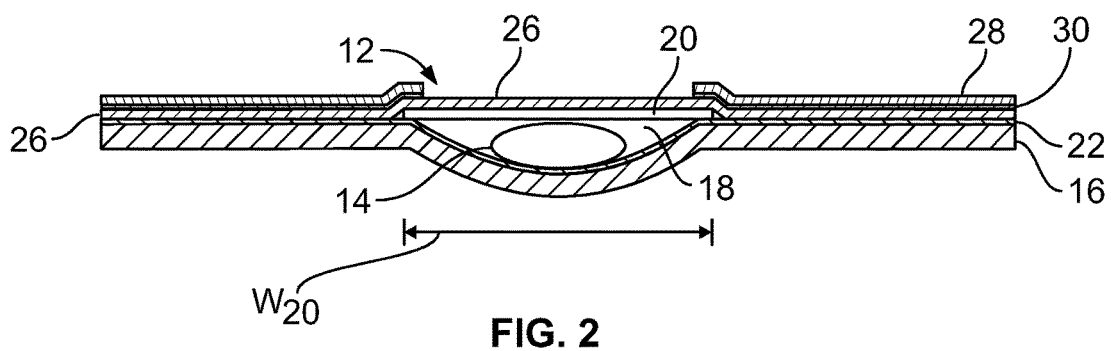
FIG. 2 is a cross-sectional view taken along line 2-2 of FIG. 1.

FIG. 2 is a cross-sectional illustration of the strip 10 of FIG. 1. The strip 10 includes a base element 16 which is formed from a foil or other high-heat transfer material. The base element 16 includes an adhesive backing (the adhesive is indicated at 22). The base element 16 has a length $L_{16}$ and a width $W_{16}$. The present base element 16 is an aluminum foil. A depression or recess 18 is formed in the foil 16. A temperature sensitive chemical 14 formulation is deposited in the recess 18.

A wicking element 20, such as a wicking paper is positioned on the base element 16 in contact with the temperature sensitive chemical 14 and extends longitudinally along the base element 16. The recess 18, temperature sensitive chemical 14 and wicking element 20 have a width (indicated, generally, collectively at $W_{20}$) and a length (indicated, generally, collectively at $L_{20}$) that is less than the width $W_{16}$ and the length $L_{16}$ of the base element 16. In this manner the recess 18, temperature sensitive chemical 14 and wicking element 20 are bounded within the lateral sides 24 of the test strip 10.

A film 26 is applied over the base element 16, temperature sensitive chemical 14, wicking element 20 and is adhered to the base element 16 by the adhesive 22. The film 26 is a transparent film, as will be discussed in more detail below. A coated paper 28, having an adhesive backing 30 is applied over the film 26. The coated paper 28 includes the window 12 that is cut out (as seen in FIG. 1) to allow for visual indication within the window 12, through the film 26.

In exemplary test strips 10, the foil element 16 with the adhesive 22 is a 3/1000 inch (3 mil) thick Avery® 1905 or 5803 foil adhesive label, commercially available from Avery Dennison Corporation of Mentor, Ohio. The adhesive 22 on the foil 16 (to adhere to the film 26) is an acrylic adhesive. The adhesive coated paper 28, 30 is an acrylic coated paper such as that commercially available from Fasson, a division of Avery Dennison, under the trade name Fasson® 19348.

The film 26 is a cast polypropylene having a thickness of about 2.0 to 2.2 mils or 3.0 to 3.2 mils, such as that commercially available from Copol International of North Sydney, Canada under the product designator HP204. The wicking material is, for example, that which is commercially available from Whatman Inc. of Piscataway, N.J. under the product identifier SS410. This wicking material is a low-ash, qualitative paper having a basis weight of about 66 grams per square meter (g/m$^2$) and a caliper or thickness of about 7.3 thousandths of an inch (mils). An alternate wicking material is that which is commercially available from Ahlstrom Corporation of Helsinki, Finland, under the product identifier 238 wicking paper or the product identifier 601 wicking paper. This wicking material is a white, smooth surface, cotton paper having a basis weight of about 186 g/m$^2$ and a caliper or thickness of about 13.3 mils.

The temperature sensitive chemical 14 is phenacetin, having a colorant added in a concentration of about 0.01 percent by weight. A present colorant is Nile Blue A.

It will be appreciated and understood by those skilled in the art that the coated paper window 12 extends over an area of the surface of the paper 28 less than the entirety of the paper 28. The width $W_{it}$ of the window is slightly less than the width $W_{20}$ of the wicking element 20.

The paper 28 also includes a marker 32 indicated at a location to which the chemical must liquefy and wick along the wicking material 20 to indicate that the proper sterilization parameters have been reached. That is, the color (in the illustrated strip 10, the color blue) must reach the mark 32 shown on the paper 28 (on the strip 10) to indicate that proper conditions have been reached for sterilization. Therefore, the marker 32 is drawn at a precalculated distance from the location of the temperature sensitive chemical 14 according to the particular sterilization parameters. In the embodiment shown, the temperature sensitive chemical 14 is arranged proximate an end 13 of the open window 12 and the marker is provided near the other end 15 of the open window 12 (FIG. 1.) In other embodiments, the temperature sensitive chemical 14 can be placed laterally between the end 13 of the open window 12 and a side 25 of the sterilization strip 10 (around the area indicated with a reference number 17 in FIG. 1), such that the temperature sensitive chemical 14 is not under the open window 12, but under the surface of the paper 28. In such embodiments, wicking element 12 is in contact with the temperature sensitive chemical 14 proximate its one end and extends laterally at least beyond the marker 32, such that the liquefied chemical can travel along the wicking element and reach the marker 32 when the proper conditions have been met for sterilization.

The illustrated sterilization test strip 10 is a Class 6 sterilization indicator. One embodiment is configured to verify sterilization at 132° C. at 4 minutes time and has a temperature tolerance of 1° C. and a time tolerance of 6 percent. The strip 10 meets the performance requirements set for Class 6 indictors set by American National Standards Institute (ANSI)/Association for the Advancement of Medical Instrumentation (AAMI)/International Organization for Standards (ISO) 11140.

It will also be appreciated by those skilled in the art that the specific temperature and time requirements may vary by jurisdiction (e.g., country) and that such requirements require differing sterilizations protocols (differing temperature/time requirements be met to indicate sterilization has occurred). Such requirements, at present, vary from about 132° C. at 4 to 135° C. at 3 minutes along with different time requirements at 134° C. (e.g., 3.5 minutes, 4 minutes, 5 minutes and 7 minutes).

It has been found that varying the type of foil adhesive and the type of wicking paper, embodiments of the present strip 10 can be configured to meet these varying requirements. Table 1, below illustrates six varying constructions and the specific temperature and time protocols that are met by these constructions. As shown, the test strips for 134° C./3.5 min, 4 min and 5 min can constructed using the same materials. In such case, the marker 32 for the test strips can be drawn at different location to indicate different time requirements. For example, the marker 32 for the test strip for 134° C./5 min is drawn further away from the temperature sensitive chemical 14 than the marker 32 of the test strip for 134° C./3.5 min.

TABLE 1

TEST STRIP CONSTRUCTIONS
AND TEMPERATURE/TIME PROTOCOLS

| Test Strip Sample No. | Temperature, Time | Foil Adhesive | Wicking Paper | Cast Polypropylene Thickness |
|---|---|---|---|---|
| 1 | 132° C., 4 min | Avery ® 5803 or Avery ® I905 | Whatman ® SS410 or Ahlstrom ® 601 | 2.0 to 2.2 mils |
| 2 | 134° C., 3.5 min | Avery ® I905 | Whatman ® SS410 or Ahlstrom ® 601 | 2.0 to 2.2 mil |
| 3 | 134° C., 4 min | Avery ® I905 | Ahlstrom ® 601 | 2.0 to 2.2 mil |
| 4 | 134° C., 5 min | Avery ® 5803 or Avery ® I905 | Ahlstrom ® 601 or Ahlstrom ® 238 | 2.0 to 2.2 mil |
| 5 | 134° C., 7 min | Avery ® 5803 | Ahlstrom ® 601 or Ahlstrom ® 238 | 3.0 to 3.2 mil |
| 6 | 135° C., 3 min | Avery ® 5803 or Avery ® I905 | Whatman ® SS410 or Ahlstrom ® 601 | 2.0 to 2.2 mil |

Figure 3:
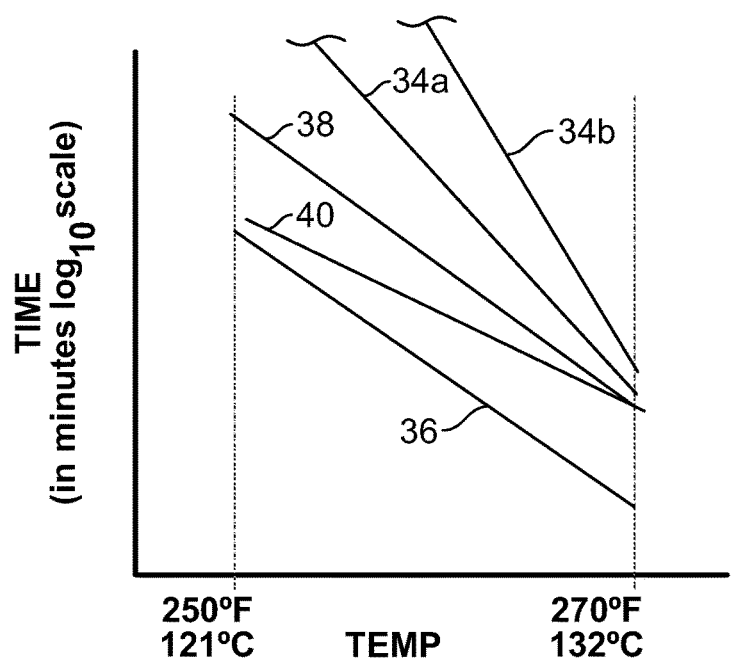
FIG. 3 is a time-temperature curve showing spore death (spore death curve) and illustrating the curves for various known test strips and embodiments of the present test strip.

Referring to FIG. 3, there is shown a time versus temperature curve (Accept curve) for embodiments of the present strip 10, Test Strips Nos. 1 (with Avery® 5803 and Whatman® SS410), 4 and 5 (with Avery® 5803 and Ahlstrom® 238) (indicated at 34a) along with the thermal death time curve for *B. stearothmophilus* live spores. The death time curve is indicated at 36. The Accept curve (that is, the corresponding time and temperature curves) for known sterilization test strips are shown at 38 and at 40. The Accept curve is the time and temperature curve at which the strip will indicate acceptable sterilization conditions have been met. The plot of the curves is shown as time in minutes ($\log_{10}$ scale) vs. temperature in degrees C. The Accept curve for Test Strips Nos. 1 (with Avery 1905 and Whatman®

SS410), 2 and 6 (with Avery® I905 and Whatman® SS410) is shown illustratively at 34*b*.

Unlike the known strips (curves 38 and 40), which are integrating (Class 5) strips, the present strip 10 is an emulating (Class 6) strip. The Class 5 strips are useful for a range of temperature/time protocols. The Class 6 strip (the present strip 10) is an emulating strip that functions at a specific, desired, predetermined temperature/time protocol, and thus provides indication at a more realistic sterilization system operating scenario.

It will thus be understood that, when exposed to steam at the predetermined temperature for the predetermined period of time, the temperature sensitive material liquefies and is drawn into the wicking material and moves to a position at or beyond the marker to indicate an acceptable level of sterilization has occurred. At temperatures below the predetermined temperature for the predetermined period of time, or at the predetermined temperature for less than the predetermined period of time, or at a temperature less than the predetermined temperature for less than the predetermined period of time, the temperature sensitive material is drawn into the wicking material and moves to a position prior to the marker to indicate that an acceptable level of sterilization has not occurred.

As will be appreciated by those skilled in the art from a study of FIG. 3, the present strip 10 provides a greater margin of safety, particularly at lower temperatures, than Class 5 or other sterilization test strips.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the invention.

What is claimed is:

1. A sterilization test strip, comprising:
   a base element formed from a thermally conductive material having a length and a width, the base element having a recess formed therein extending along about a longitudinal centerline thereof, the recess formed within the base material less than the length and the width of the base material, and the base element having an adhesive backing, wherein the base element and the adhesive backing are formed from a foil adhesive label including an aluminum foil and an acrylic adhesive;
   a temperature sensitive material deposited in the recess;
   a wicking material positioned at least in part in contact with the temperature sensitive material and positioned at least in part within the recess, the wicking material extending less than the length and width of the base element;
   a film positioned over the base element, the wicking material and the temperature sensitive material, wherein the film is formed from a cast polypropylene;
   a coated paper disposed over the film such that the temperature sensitive material and the wicking material are arranged between the adhesive backing and the film, the coated paper including a window therein; and
   a marker disposed on the sterilization test strip,
   wherein when exposed to steam at a predetermined temperature for a predetermined period of time, the temperature sensitive material liquefies and is drawn into the wicking material and moves to a position at or beyond the marker to indicate an acceptable level of sterilization has occurred, and wherein at a temperature less than the predetermined temperature for the predetermined period of time, or at the predetermined temperature for less than the predetermined period of time, or at a temperature less than the predetermined temperature for a period of time less than the predetermined period of time, the temperature sensitive material is drawn into the wicking material and moves to a position prior to the marker to indicate that the acceptable level of sterilization has not occurred, wherein the marker is disposed at a predetermined distance from the temperature sensitive material such that the temperature sensitive material moves to a position at or beyond the marker to indicate an acceptable level of sterilization after the test strip is exposed to steam at the predetermined temperature for the predetermined period of time, wherein the predetermined time and the predetermined period are selected from 132° C. for 4 minutes, 134° C. for 3.5 minutes, 134° C. for 4 minutes, 134° C. for 5 minutes, 134° C. for 7 minutes, and 135° C. for 3 minutes.

2. The test strip of claim 1 wherein the temperature sensitive material is phenacetin.

3. The test strip of claim 2 wherein the phenacetin has a dye added thereto.

4. The test strip of claim 3 wherein the dye is Nile Blue present in a concentration of about 0.01 percent by weight of the temperature sensitive material.

5. The test strip of claim 1, wherein the cast polypropylene has a thickness of about 2.0 to 2.2 mils.

6. The test strip of claim 1, wherein the cast polypropylene has a thickness of about 3.0 to 3.2 mils.

7. The test strip of claim 1 wherein the coated paper has an adhesive backing.

8. The test strip of claim 1 wherein the coated paper has an acrylic coating thereon.

9. The test strip of claim 1, wherein the foil adhesive has a total thickness of about 3 mil; wherein the wicking material is formed from a low-ash, qualitative paper having a basis weight of about 66 g/m$^2$ and a thickness of about 7.3 mil, or a cotton paper having a basis weight of about 186 g/m$^2$ and a thickness of about 13.3 mil; wherein the film is formed from a cast polypropylene having a thickness of about 2.0 mil to about 2.2 mil; and wherein the marker is disposed at a predetermined distance from the temperature sensitive material such that the temperature sensitive material moves to a position at or beyond the marker to indicate an acceptable level of sterilization after the test strip is exposed to steam at 132° C. for 4 minutes.

10. The test strip of claim 1, wherein the foil adhesive has a total thickness of about 3 mil; wherein the wicking material is formed from a low-ash, qualitative paper having a basis weight of about 66 g/m$^2$ and a thickness of about 7.3 mil, or a cotton paper having a basis weight of about 186 g/m$^2$ and a thickness of about 13.3 mil; wherein the film is formed from a cast polypropylene having a thickness of about 2.0 mil to about 2.2 mil; and wherein the marker is disposed at a predetermined distance from the temperature sensitive material such that the temperature sensitive material moves to a position at or beyond the marker to indicate an acceptable level of sterilization after the test strip is exposed to steam at 134° C. for 3.5 minutes.

11. The test strip of claim 1, wherein the foil adhesive has a total thickness of about 3 mil; wherein the wicking material is formed from a cotton paper having a basis weight of about 186 g/m² and a thickness of about 13.3 mil; wherein the film is formed from a cast polypropylene having a thickness of about 2.0 mil to about 2.2 mil; and wherein the marker is disposed at a predetermined distance from the temperature sensitive material such that the temperature sensitive material moves to a position at or beyond the marker to indicate an acceptable level of sterilization after the test strip is exposed to steam at 134° C. for 4 minutes.

12. The test strip of claim 1, wherein the foil adhesive has a total thickness of about 3 mil; wherein the wicking material is formed from a cotton paper having a basis weight of about 186 g/m² and a thickness of about 13.3 mil; wherein the film is formed from a cast polypropylene having a thickness of about 2.0 mil to about 2.2 mil; and wherein the marker is disposed at a predetermined distance from the temperature sensitive material such that the temperature sensitive material moves to a position at or beyond the marker to indicate an acceptable level of sterilization after the test strip is exposed to steam at 134° C. for 5 minutes.

13. The test strip of claim 1, wherein the foil adhesive has a total thickness of about 3 mil; wherein the wicking material is formed from a cotton paper having a basis weight of about 186 g/m² and a thickness of about 13.3 mil; wherein the film is formed from a cast polypropylene having a thickness of about 3.0 mil to about 3.2 mil; and wherein the marker is disposed at a predetermined distance from the temperature sensitive material such that the temperature sensitive material moves to a position at or beyond the marker to indicate an acceptable level of sterilization after the test strip is exposed to steam at 134° C. for 7 minutes.

14. The test strip of claim 1, wherein the foil adhesive has a total thickness of about 3 mil; wherein the wicking material is formed from a low-ash, qualitative paper having a basis weight of about 66 g/m² and a thickness of about 7.3 mil, or a cotton paper having a basis weight of about 186 g/m² and a thickness of about 13.3 mil; wherein the film is formed from a cast polypropylene having a thickness of about 2.0 mil to about 2.2 mil; and wherein the marker is disposed at a predetermined distance from the temperature sensitive material such that the temperature sensitive material moves to a position at or beyond the marker to indicate an acceptable level of sterilization after the test strip is exposed to steam at 135° C. for 3 minutes.

* * * * *

UNITED STATES PATENT AND TRADEMARK OFFICE
CERTIFICATE OF CORRECTION

PATENT NO. : 9,623,134 B1  
APPLICATION NO. : 14/852230  
DATED : April 18, 2017  
INVENTOR(S) : Harry Bala et al.

Page 1 of 1

It is certified that error appears in the above-identified patent and that said Letters Patent is hereby corrected as shown below:

In the Specification

Column 5, Line 24, "Wit" to read as --W20--.

Column 6, Line 67, "1905" to read as --I905--.

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*